United States Patent [19]
Zanzucchi et al.

[11] Patent Number: 5,643,738
[45] Date of Patent: Jul. 1, 1997

[54] METHOD OF SYNTHESIS OF PLURALITY OF COMPOUNDS IN PARALLEL USING A PARTITIONED SOLID SUPPORT

[75] Inventors: Peter John Zanzucchi, West Windsor Township, Mercer County; Satyam Choudary Cherukuri, Cranbury; Sterling Edward McBride, Lawrence Township, Mercer County, all of N.J.; Amrit Kaur Judd, Belmont, Calif.

[73] Assignee: David Sarnoff Research Center, Inc., Princeton, N.J.

[21] Appl. No.: 454,781

[22] Filed: May 31, 1995

Related U.S. Application Data

[62] Division of Ser. No. 338,703, Nov. 10, 1994, Pat. No. 5,585,069.

[51] Int. Cl.$^6$ .............................. C12Q 1/68; C07H 21/00; C08F 283/00

[52] U.S. Cl. .................. 435/6; 536/25.3; 536/25.31; 422/131; 422/134; 525/54.11

[58] Field of Search .................... 435/6; 436/518; 536/24.3, 25.3, 25.31; 422/131, 134; 427/2.13; 525/54.11

[56] References Cited

U.S. PATENT DOCUMENTS

| | | | |
|---|---|---|---|
| 3,615,241 | 10/1971 | Low et al. | 23/259 |
| 4,385,115 | 5/1983 | de Zabala et al. | 435/33 |
| 4,676,274 | 6/1987 | Brown | 137/806 |
| 4,753,775 | 6/1988 | Ebersole et al. | 422/81 |
| 4,756,884 | 7/1988 | Hillman et al. | 422/73 |
| 4,891,120 | 1/1990 | Sethi et al. | 204/299 R |
| 4,908,112 | 3/1990 | Pace | 204/299 R |
| 4,948,961 | 8/1990 | Hillman et al. | 250/252.1 |
| 4,963,498 | 10/1990 | Hillman et al. | 436/69 |
| 4,966,646 | 10/1990 | Zdeblick | 156/633 |
| 5,006,749 | 4/1991 | White | 310/323 |
| 5,026,773 | 6/1991 | Steel | 525/54.11 |
| 5,037,882 | 8/1991 | Steel | 525/54.11 |
| 5,053,454 | 10/1991 | Judd | 525/54.11 |
| 5,073,029 | 12/1991 | Eberly et al. | 356/432 |
| 5,140,161 | 8/1992 | Hillman et al. | 250/341 |
| 5,141,868 | 8/1992 | Shanks et al. | 435/288 |
| 5,143,854 | 9/1992 | Pirrung et al. | 436/518 |
| 5,144,139 | 9/1992 | Hillman et al. | 250/341 |
| 5,147,607 | 9/1992 | Mochida | 422/57 |
| 5,164,598 | 11/1992 | Hillman et al. | 250/341 |
| 5,175,209 | 12/1992 | Beattie et al. | 525/54.11 |
| 5,176,203 | 1/1993 | Larzul | 165/61 |
| 5,194,133 | 3/1993 | Clark et al. | 204/299 R |
| 5,204,525 | 4/1993 | Hillman et al. | 250/252.1 |
| 5,229,297 | 7/1993 | Schnipelsky et al. | 436/94 |
| 5,237,016 | 8/1993 | Ghosh et al. | 525/329.4 |
| 5,250,263 | 10/1993 | Manz | 422/81 |
| 5,277,754 | 1/1994 | Hadimioglu et al. | 156/644 |
| 5,288,463 | 2/1994 | Chemelli | 422/58 |
| 5,288,468 | 2/1994 | Church et al. | 422/116 |
| 5,296,114 | 3/1994 | Manz | 204/180 |
| 5,304,487 | 4/1994 | Wilding et al. | 435/291 |
| 5,324,483 | 6/1994 | Cody et al. | 422/131 |
| 5,324,633 | 6/1994 | Fodor et al. | 435/6 |
| 5,359,115 | 10/1994 | Campbell et al. | 558/110 |
| 5,368,823 | 11/1994 | McGraw et al. | 422/134 |
| 5,384,261 | 1/1995 | Winkler et al. | 436/518 |
| 5,412,087 | 5/1995 | McGall et al. | 536/24.3 |
| 5,420,328 | 5/1995 | Campbell | 558/110 |
| 5,424,186 | 6/1995 | Fodor et al. | 435/6 |
| 5,463,564 | 10/1995 | Agrafiotis et al. | 364/496 |
| 5,472,672 | 12/1995 | Brennan | 422/131 |
| 5,474,796 | 12/1995 | Brennan | 427/2.13 |
| 5,480,614 | 1/1996 | Kamahori | 422/70 |

FOREIGN PATENT DOCUMENTS

| | | |
|---|---|---|
| 0 198 413 | 10/1986 | European Pat. Off. . |
| 0 402 995 | 12/1990 | European Pat. Off. . |
| 0 430 248 | 6/1991 | European Pat. Off. . |
| 0 483 117 | 4/1992 | European Pat. Off. . |
| 2248840 | 6/1990 | United Kingdom . |
| WO90/09596 | 8/1990 | WIPO . |
| WO91/16966 | 11/1991 | WIPO . |
| WO92/10092 | 6/1992 | WIPO . |
| WO93/06121 | 4/1993 | WIPO . |
| WO93/22058 | 11/1993 | WIPO . |
| WO94/05414 | 3/1994 | WIPO . |
| WO94/10128 | 5/1994 | WIPO . |
| WO95/12608 | 5/1995 | WIPO . |

OTHER PUBLICATIONS

Dasgupta, et al., Electroosmosis: A Reliable Flud Propulsion System for Flow Injection Analysis, Anal. Chem. 66:1792–1798, 1994.

Jacobson, et al., Precolumn Reactions with Electrophoretic Analysis Integrated on a Microchip, Anal. Chem. 66:4127–4132, 1994.

Richter, et al., A Micromachined Electrohydrodynamic (EHD) Pump, Sensors and Actuators A, 29:159–168, 1991.

Bart, et al., Microfabricated Electrohydrodynamic Pumps, Sensors and Actuators, A21–A23:193–197, 1990.

Melcher, Traveling–Wave Induced Electroconvection, The Physics of Fluids, 9:1548–1555, 1966.

Pickard, Ion Drag Pumping. I. Theory, J. Applied Physics 34:246–250, 1963.

Pickard, Ion Drag Pumping. II. Experiment, J. Applied Physics, 34:251–258, 1963.

Stuetzer, Ion Drag Pumps, J. Applied Physics, 31:136–146, 1960.

Petersen, Silicon as a Mechanical Material, Proceedings of The IEEE, 70:420–457, 1982.

Tracey, et al., Microfabricated Microhaemorheometer, pp. 82–84, 1991.

Medynski, Synthetic Peptide Combinatorial Libraries, Bio/Technology, 12:709–710, 1994.

(List continued on next page.)

Primary Examiner—Stephanie W. Zitomer
Assistant Examiner—Amy Atzel
Attorney, Agent, or Firm—William J. Burke

[57] ABSTRACT

Methods are provided for synthesizing a plurality of compounds in parallel. The methods use cross-over channels for moving samples from a reservoir of starting materials into a plurality of wells. The movement is achieved, for example, using an electrokinetic pump.

24 Claims, 10 Drawing Sheets

OTHER PUBLICATIONS

Jacobson, et al., Effects of Injection Schemes and Column Geometry on the Performance of Microchip Electrophoresis Devices, Anal. Chem. 66:1107–1113, 1994.

Megregany, Microelectromechanical Systems, Circuits and Devices, Jul. 1993, pp. 14–22.

Fisher, Microchips for Drug Compounds, New York Times, Mar. 3, 1991.

Fodor, et al., Light–Directed, Spatially Addressable Parallel Chemical Synthesis, Science, 251:767–773, 1991.

The Silver Shotguns, The Economist, Dec. 14–20, 1991.

Howe, et al., Silicon Micromechanics; Sensors and Actuators on a Chip, IEEE Spectrum, Jul. 1990, pp. 29–35.

Angell, et al., Silicon Micromechanical Devices, Scientific American 248:44–55, 1983.

Andreas Manz et al., *Trends in Analytical Chemistry*, 10(5):144–148 (1991).

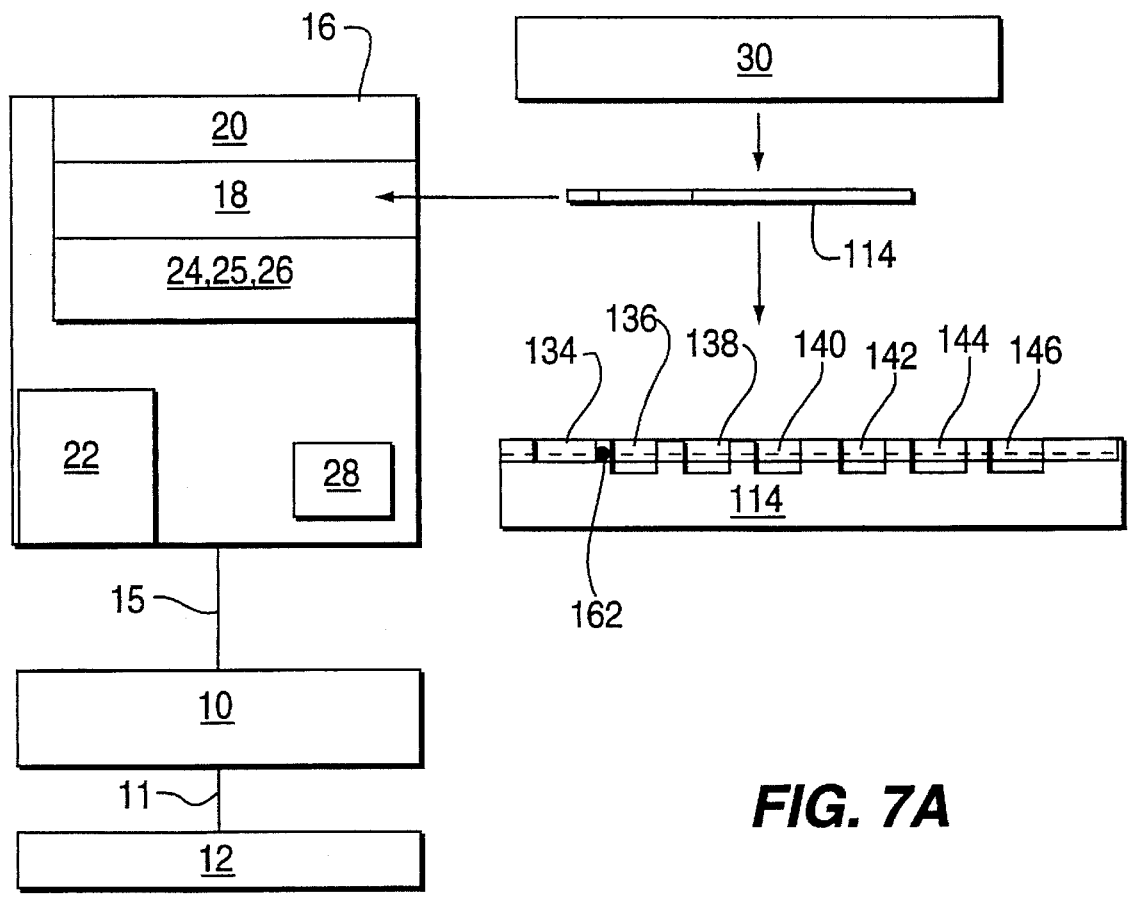
FIG. 7A
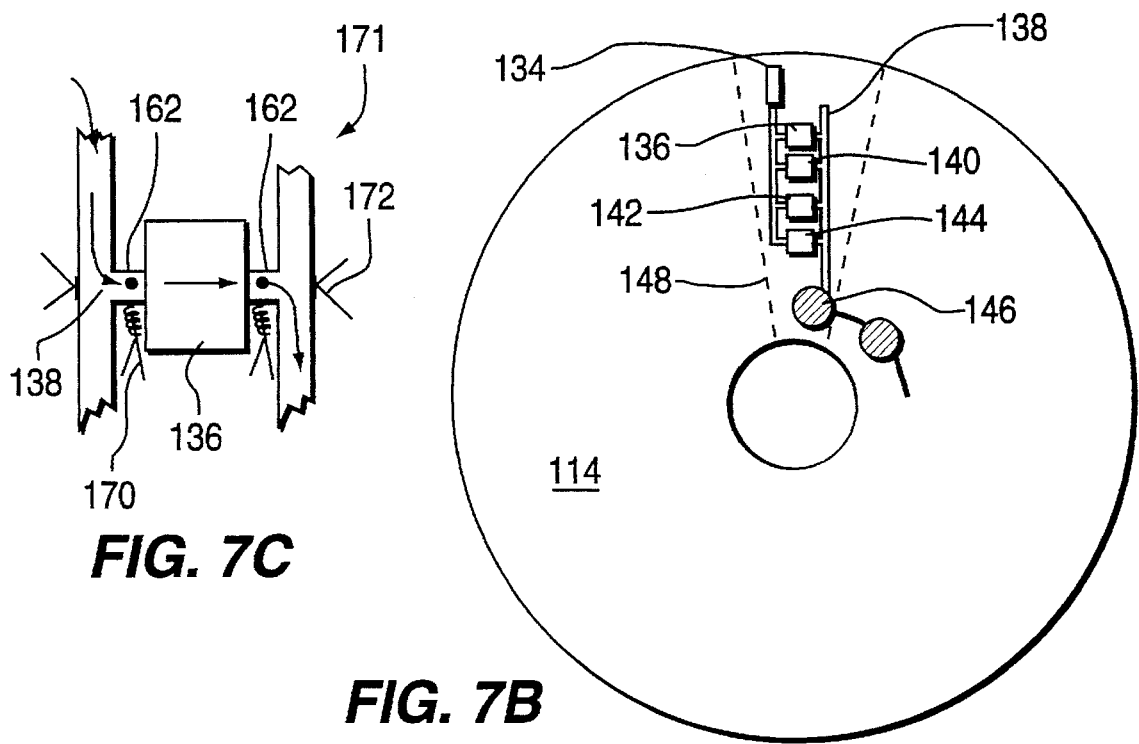
FIG. 7C
FIG. 7B

METHOD OF SYNTHESIS OF PLURALITY OF COMPOUNDS IN PARALLEL USING A PARTITIONED SOLID SUPPORT

This is a division of application Ser. No. 08/338,703, filed Nov. 10, 1994, now U.S. Pat. No. 5,585,069.

This invention relates to a system comprising a partitioned microelectronic and fluidic array. More particularly, this invention relates to a system including an array of microelectronic and fluid transfer devices for carrying out various processes, including syntheses, screening and chemical diagnostic assays, in parallel, and method of making the array.

BACKGROUND OF THE DISCLOSURE

Traditional methods of making a homologous series of compounds, or the testing of new potential drug compounds comprising a series of like compounds, has been a slow process because each member of the series or each potential drug must be made individually and tested individually. For example, a plurality of potential drug compounds is tested by using an agent to test a plurality of materials that differ perhaps only by a single amino acid or nucleotide base, or have a different sequence of amino acids or nucleotides.

Recently the process has been improved somewhat combining the synthesis of various compounds having potential biological activity, for example, and traditional semiconductor techniques. A semiconductor or dielectric substrate for example is coated with a biologic precursor having amino groups with a light-sensitive protective chemical attached thereto, and a series of masks are placed over the substrate, each mask having an opening. A coupling agent, such as a photosensitive amino acid, is illuminated through the opening, forming a particular compound by reaction with the amino compound. Additional masks are used with different coupling agents to form an array of different peptides on the substrate which array can then be tested for biologic activity. Suitably this is done by exposure of the array to a target molecule, such as an antibody or a virus. The array is exposed to a biologic receptor having a fluorescent tag, and the whole array is incubated with the receptor. If the receptor binds to any compound in the array, the site of the fluorescent tag can be detected optically. This fluorescence data can be transmitted to a computer which can compute which compounds reacted and the degree of reaction. This technique permits the synthesis and testing of thousands of compounds in days rather than in weeks or even months.

However, the synthesis of each coupling reaction is not always complete, and the yield decreases as the length of the biopolymer increases. The process of aligning a plurality of masks and forming openings in the masks in sequence requires careful alignment and takes time.

The above synthesis is made possible by two other recent technical developments that allow various manipulations and reactions on a planar surface. One is the detection and analysis of DNA fragments and their identification by reaction with specific compounds. Probes, RNA and DNA fragments can be resolved, labeled and detected by high sensitivity sensors. The presence or absence of DNA fragments can identify diseased cells for example.

Another step forward is the ability to separate materials in a microchannel, and the ability to move fluids through such microchannels. This is made possible by use of various electro-kinetic processes such as electrophoresis or electro-osmosis. Fluids may be propelled through very small channels by electro-osmotic forces. An electro-osmotic force is built up in the channel via surface charge buildup by means of an external voltage that can "repel" fluid and cause flow. This surface charge and external voltage produces an electro-kinetic current that results in fluid flow along the channel. Such electro-kinetic processes are the basis for a device described by Pace in U.S. Pat. No. 4,908,112 for example.

Thus real progress has been made using electrophoresis and/or electro-osmosis to move very small amounts of materials along microchannels. Such movement can be used for synthesizing very small samples of potential drug compounds in an array and testing very small amounts of materials for bioactivity. Further progress in fully automating the fluidic processes will result in the synthesis and testing of vast numbers of compounds for bioactivity of all types, which information can be made available for future drug selection and will greatly reduce the time and expense of such testing.

SUMMARY OF THE INVENTION

The system of the invention comprises a device array of micron sized wells and connecting channels in a substrate that interfaces with a station for dispensing fluids to and collecting fluids from, the array, and for performing electro-optic measurements of material in the wells. The station is also connected to control apparatus means to control the fluid flow to the channels and wells and to collect measurement data from the substrate. The above elements are interdependent and together can perform a variety of tasks in parallel.

The individual wells of the array and their sequence can be varied depending on the synthesis or analysis to be performed. Thus the function of the arrays can be readily changed, with only the additional need to choose suitable interface means for monitoring and controlling the flow of fluids to the particular array being used and the test or synthesis to be performed.

In one embodiment the above system can be used to perform various clinical diagnostics, such as assays for DNA in parallel, using the known protocols of the polymerase chain reaction (PCR), primers and probe technology for DNA assay. In another embodiment the above system can be used for immunoassays for antibodies or antigens in parallel for screening purposes. In still other embodiments, the synthesis of a series of chemical compounds, or a series of peptides or oligonucleotides, can be performed in parallel. Each well in the array is designed so to accomplish a selected task in appropriate modules on a substrate, each module containing the number of wells required to complete each task. The wells are connected to each other, to a sample source and to a source of reagent fluids by means of connecting microchannels. This capability permits broad based clinical assays for disease not possible by sequential assay, permits improvement in statistics of broad based clinical assays such as screening of antibodies because of the parallelism, permits a reduction in costs and an improvement in the speed of testing, and permits improved patient treatments for rapidly advancing disease.

The array is formed in a suitable dielectric substrate and the channels and wells are formed therein using maskless semiconductor patterning techniques. The station and control means, such as a computer, use existing technology that includes commercially available apparatus.

The present device array uses active control to move fluids across the array, reducing the time required for synthesis and screening. Further, large biopolymers of all types can be synthesized and processed while maintaining high purity of the synthesized compounds. The present microlaboratory arrays may be fully automated, enabling the rapid transfer of samples, precursors and other movement of fluids into the array, from one well to another well, and to enable the measurement of assays and the complete control of processing parameters such as temperature control.

BRIEF DESCRIPTION OF THE DRAWING

FIG. 7A is an exploded schematic view of another embodiment of the present invention adapted to perform immunological assays.

FIG. 7B is a top view illustrating a module on the microlaboratory disc of FIG. 7A.

FIG. 7C is a cross sectional view of a control means for moving fluids in the channels and from one well to another.

DETAILED DESCRIPTION OF THE INVENTION

The invention will be first described by reference to FIG. 1A, which illustrates the parts of an illustrative system of the invention configured to perform DNA screening diagnostics.

Figure 1A:
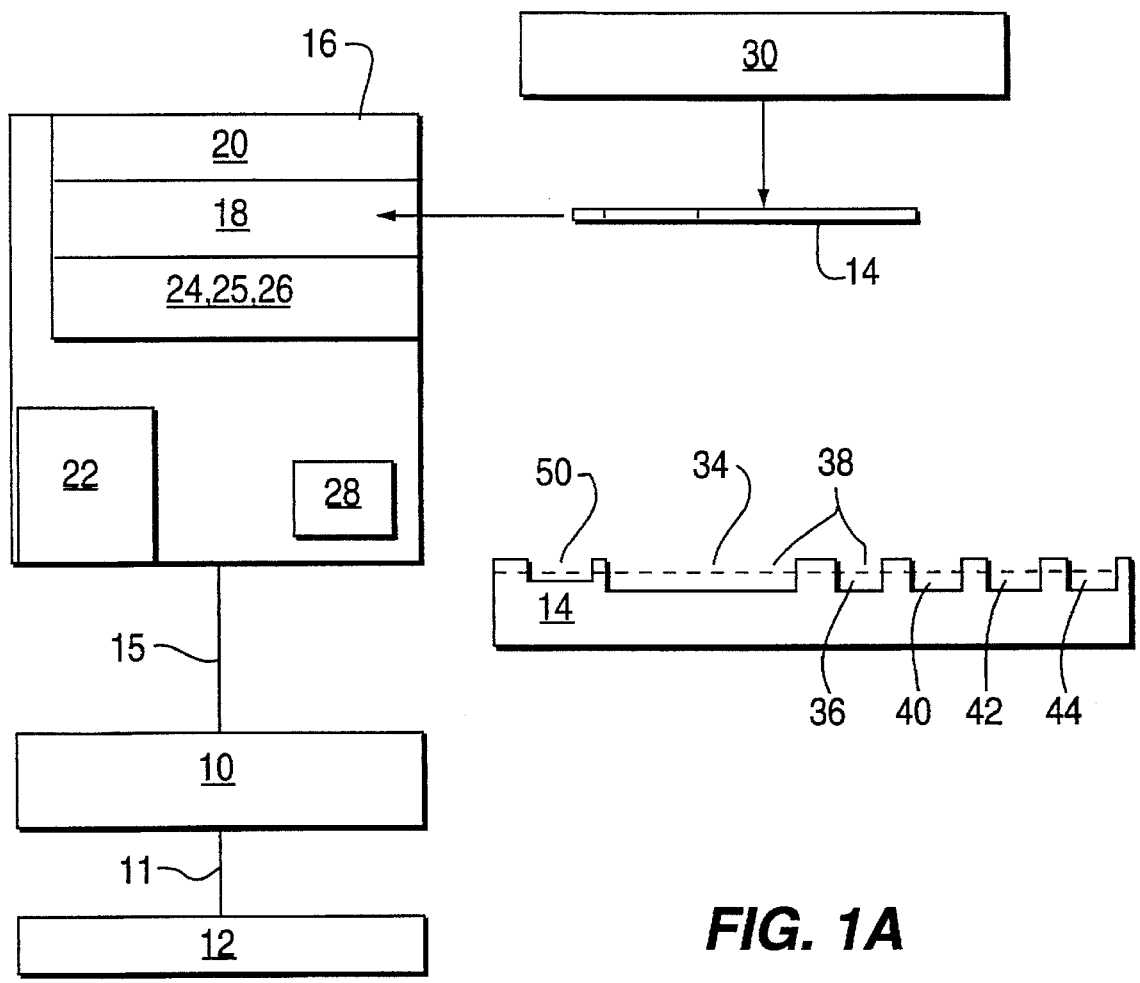
FIG. 1A is an exploded schematic diagram of the parts of the system of the invention adapted for performing clinical assays.

The system of FIG. 1A includes a computer 10, electrically connected via line 11 to peripheral apparatus, such as a modem or printer 12, which computer 10 is programmed to give instructions to a microlaboratory disc 14 and to record test results obtained therefrom. The computer 10 is electrically connected to a station 16 via line 15. The station 16 includes a microlaboratory disc support 18, support tubing 20 for loading test materials and reagents onto the microlaboratory disc 14, pumps 22 for moving fluids to particular destinations on the disk 14, one or more light sources 24, an optical fiber 25 and one or more light detectors 26. The optical fibers 25 is operative to transmit light from the light source 24 to the detector 26. One or more containers 28 for waste fluids and the like are also housed in the station 16.

A small volume of a fluid to be tested, such as a whole blood or other DNA-containing fluid sample, is loaded into the system via a loading system 30. The system 30 may house one or more capillary tubes 32, illustrated in FIG. 3, containing a sample which is connected to a loading capillary channel 34 etched into the surface of the microlaboratory disc 14. The loading capillary tube 32 is inserted into the capillary loading channel 34 horizontally. The sample is moved into the capillary loading channel 34 and the fluid sample is then moved to a first well 36 on the disc 14. Alternately, a loading channel 50 for vertical insertion into the loading channel 34 can also be used to load the sample.

Figure 1B:
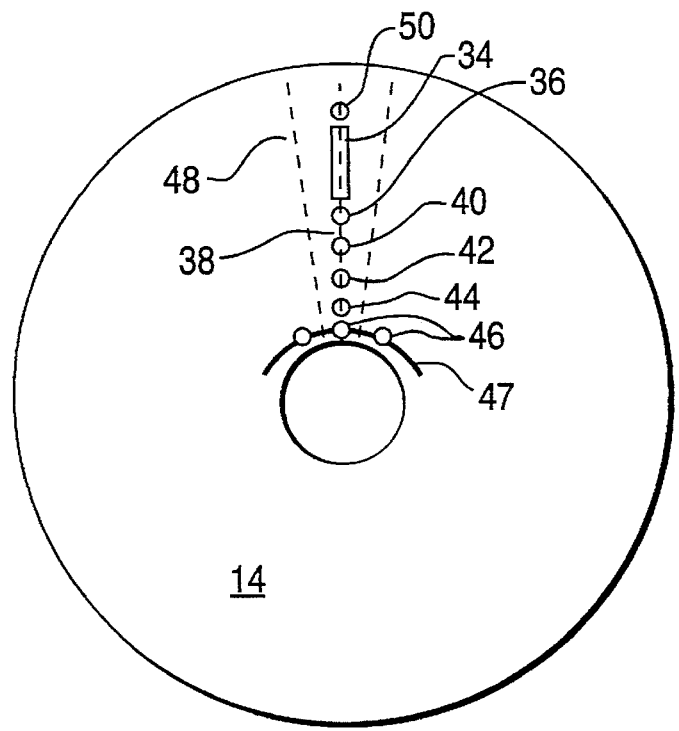
FIG. 1B is a top view of a substrate of the invention illustrating a single module formed therein.
Figure 2:
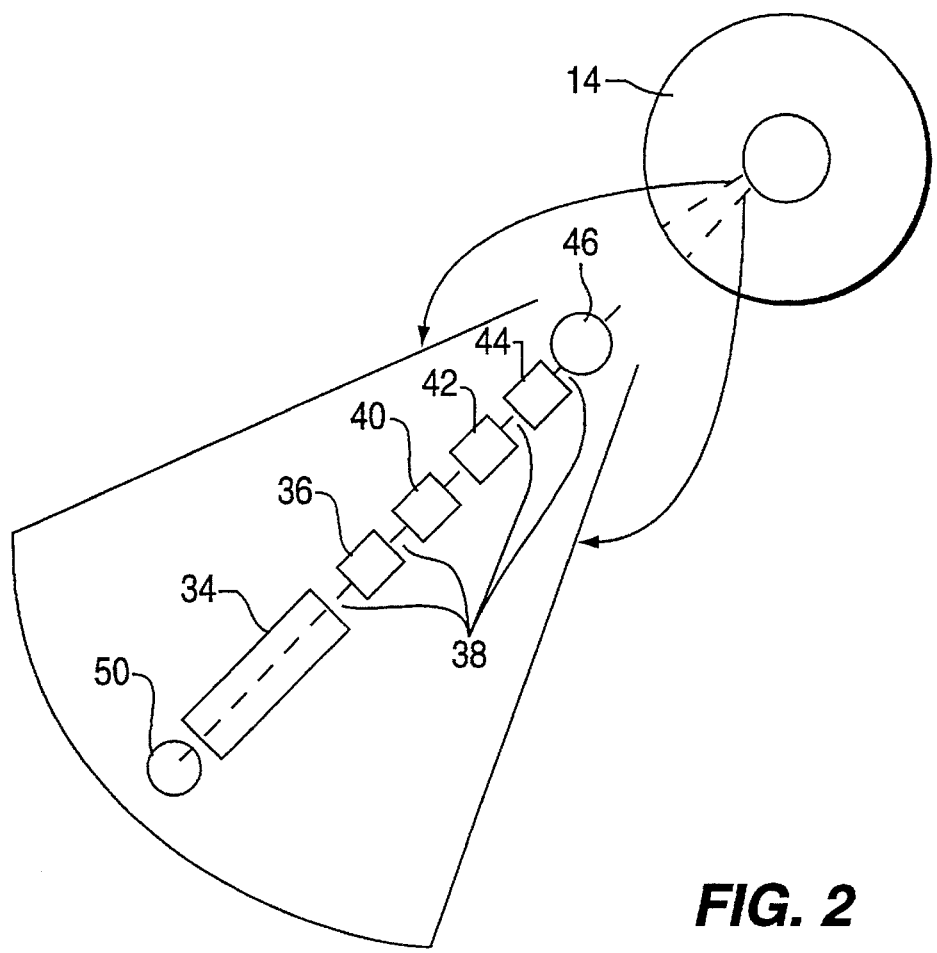
FIG. 2 is an exploded top view of an illustrative module of the invention.

FIG. 1B and FIG. 2 illustrate a particular module comprising a plurality of wells 36, 40, 42 and 44 connected by a channel 38, shown by a dashed line, on a microlaboratory disc 14 of the invention. Each module is connected to a well 46 that collects excess-or waste fluids from the respective module. These waste fluids are collected and moved to the waste containers 28 in the station 16.

The sample is treated sequentially in a series of wells including first well 36. For example, in the first well 36 the whole blood sample is transferred from the capillary loading channel 34, filtered and lysed to separate the white and red corpuscles, and the DNA is isolated from the white blood cells. The DNA sample is then moved out of the first well 36 through a connecting channel 38 that connects all of the wells of a single module, and into a second well 40. In the second well 40 the DNA is separated into single strands and amplified using the well known PCR method. The treated sample is then moved out of the second well 40 via the connecting channel 38 and into a third well 42. In the third well 42 the DNA is assayed by known probe hybridization techniques, The DNA assay is detected and evaluated in the fourth well 44. Thus the determination of DNA in a particular blood sample is performed in a series of four wells connected by a channel. Lastly excess reagents and the like are collected in the fifth well 46 that is common to all of the modules in the microlaboratory array 14, and is transferred into the waste collection system 28 of the station 16.

The combination of a loading channel 34 or 50, the wells 36, 40, 42, 44 and 46 and the connecting channel 38 make up one module 48 on the test microlaboratory disc 14. A single module on a microlaboratory disc 14 is shown in top view in FIG. 1B within the dashed lines. As will be explained hereinbelow, a plurality of modules are formed in the microlaboratory disc 14 so that tests can be performed on a large number of the modules 48 in parallel.

The particular sequence of channels and wells of the module shown in FIGS. 1A, 1B and FIG. 2 lends itself to the detection of pathogenic bacteria in blood or other DNA-containing fluids using the DNA assay protocols of Greisen et al, see "PCR Primers and Probes for the 16S rRNA Gene of Most Species of Pathogenic Bacteria, Including Bacteria Found in Cerebrospinal Fluid", J. Clinical Microbiology 32

(2), pp335–351 (1994). Since the disc 14 can be arranged to form a plurality of up to 1500 parallel modules, broad DNA screening can be conducted in parallel that might not be possible using a system of sequential assays. Since a large array of parallel tests can be done at the same time, the time required to obtain meaningful results is also reduced, and consequently costs are reduced. Further, the statistics of broad based screening can be improved. In addition the system of the invention provides the ability to detect mutant DNA such as is found in oncological diseases.

The station 16 includes a fiber optic assembly 25 and one or more light sources 24 and one or more detectors 26 (not shown) that address the system loading channel 34 or 50 and measures the transmittance or absorbance of material in the channel 34 or 50 and the first well 36, such as a blood or other fluid sample. The fiber optic assembly 25 can verify the presence or absence of materials in the channel 34 or 50 or the well 36, and quantify their amounts by transmitting the measurement data to the computer 10. Suitable lasers and photodetectors are available commercially. Fiber optic adaptors to support the optical fiber are commercially available. These adaptors may also include a lens for efficient transfer of light from the light source into the fiber.

Preselected substrates, designed either for modular parallel or array processing, can be placed on the substrate holder 18 in the station 16. After suitable modification of the software in the computer 10 or choice of other driving means able to monitor a particular sequence of steps for control of reagents to carry out the processes in each module of the microlaboratory 14, entirely different tests and processes can be carried out in the system of the invention. Thus the microlaboratory array 14 is individually designed for a variety of assay, measurement and synthesis tasks, and only the module configuration and the driving means needs to be changed in the system when a different task is to be performed.

A circuit of thin film transistors (not shown) can be formed on the front or back of the glass or other substrate 14 to provide power to the wells via leads and electrodes explained further hereinafter, and to connect them with the driving means such as the computer 10, so as to move liquids along the array. Pins can also be formed in the glass substrate which are addressable by logic circuits on the support 18 that are connected to the computer 10 for example. These transistors and logic circuits will also be in contact with the substrate 14 on the support 18 to provide an interface between the microlaboratory disc 14 and the computer 10.

Figure 3:
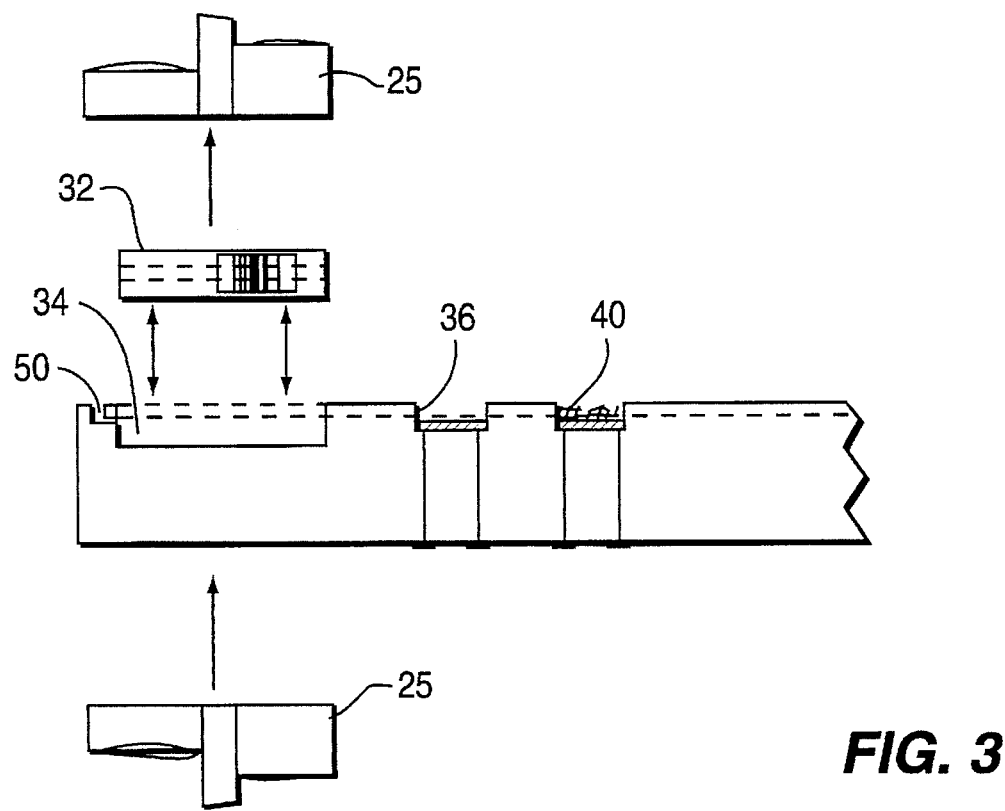
FIG. 3 is an exploded cross sectional view of the optical transmission and detection system of the invention.

The system loader 30 is situated outside of the station 16 and may be connected to a loading capillary tube 32, as shown in FIG. 3, suitably having an inner diameter of about 200 microns and an outer diameter of about 600–700 microns. The capillary tube 32 can be pretreated to eliminate surface adsorption of proteins and related bio materials a known manner, for example similar to the methods disclosed by Cobb, "Electrophoretic Separations of Proteins in Capillaries with Hydrolytically Stable Surface Structures", Anal. Chem. 62, (1990) pp 2478–2483. All of the sample material is loaded into the system via the system loader 30. The system capillary tube 32 can be loaded horizontally directly into the microlaboratory disk 14 via the loading channel 34. The sample is identified, as with a bar code or other high density code affixed to the loading capillary tube 32 as by its position on the disc array. As the sample loading tube 32 is inserted into the loading channel 34, a sealant, which can be adhered to the edge of the capillary sample tube 32 or to the loading channel 34, seals the capillary tube 32 to the channel 34. Alternately, the sample capillary tube 32 can be inserted into a separate loading channel 50 vertically, which permits a smaller loading channel to be used, but the sample may enter into the connecting channel 38 through force of gravity rather than via a controlled pump feed from the pumps 22 in the station 16. This alternate configuration 50 is also shown in FIGS. 1–3.

The heart of the present system is the parallel modular microlaboratory disc 14, shown in a side view in FIG. 1A and in a top view in FIG. 1B. FIGS. 1B and 2 illustrate a single module on a microlaboratory disc 14, which is suitably about 8.5 cm in diameter.

Each module of the microlaboratory array is made up of one or more wells connected by a channel, in turn connected to the loading capillary tube. The microlaboratory disc 14 itself can be made from glass, fused silica, quartz or a silicon wafer for example, suitably about 1 millimeter thick, that is able to be finely and controllably etched using semiconductor techniques and a suitable etchant such as HF. High quality glasses such as a high melting borosilicate glass or a fused silica, will be preferred for their UV transmission properties when any of the processes or measurements carried out in the wells or channels use light based technologies. The module 48 illustrated in FIG. 1B comprises four connecting wells, but this is by way of example only, and more or fewer wells can be present depending on the tests or syntheses to be performed in each module, and the number of steps required to perform them, as will be further described hereinbelow.

The desired number of wells are etched into the microlaboratory disk sufficient to perform the sequence of steps to be used for testing or synthesis for that particular microlaboratory disc. All of the wells in each module are connected together via one or more channels. The modular design permits efficient placement of each module on the disc substrate. When only a few wells are required for each module, two modules can be formed in each radial slice of the disc (not shown), thereby doubling the number of modules that can be etched into a single microlaboratory disk 14. Thus for an 8.5 cm diameter disk, an array of 267 single modules or 534 double modules can be readily made. When the sample is inserted vertically into the loading channel 50, which takes up less area of the substrate, additional modules can be accommodated on a single microlaboratory disc, and up to 1500 modules can be formed on a single microlaboratory disk 14. Each of the modules is connected to the system loading system 30, thus permitting parallel processing in all of the modules.

Excess fluids and waste materials for all of the modules are passed into a center well 46. A plurality of wells 46 may be connected to each other by means of a common channel 47 (FIG. 1B). A sealed tubing on the back of the substrate 14 provides an exit channel for these excess fluids that can be passed into the waste container 28 in the station 16. Thus only one exit channel 47 needs to be provided for each microlaboratory array.

The wells of the microlaboratory disc 14 can be made by the following procedure. A glass substrate disc 14 is coated sequentially on both sides with a thin chromium layer and a gold film about 1000 angstroms thick in known manner, as by evaporation or chemical vapor deposition (CVD), to protect the disc from subsequent etchants. A two micron layer of a photoresist, such as Dynakem EPA of Hoechst-Celanese Corp. is spun on and the photoresist is exposed, either using a mask or using square or rectangular images, suitably using an MRS 4500 panel stepper of MRS Technology, Inc. After developing the resist to form openings therein, and baking the resist to remove the solvent, the gold layer in the openings is etched away using a standard etch of 4 grams of KI and 1 gram of iodine ($I_2$) in 25 ml of water. The underlying chromium layer is then separately etched using an acid chromium etch, such as KTI Chrome Etch of KTI Chemicals, Inc. The glass substrate is then etched in an ultrasonic bath of $HF$—$HNO_3$—$H_2O$ in a ratio by volume of 14:20:66. The use of this etchant in an ultrasonic bath produces vertical sidewalls for the various wells. Etching of the wells is continued until the desired depth of the well is obtained, suitably about 200–750 microns deep, depending upon the functions to be performed in the well.

The connecting channel 38, suitably about 200 microns in width and 50–100 microns deep, is then etched between the wells, when the remaining photoresist and chromium-gold layer is removed.

Figure 4A:
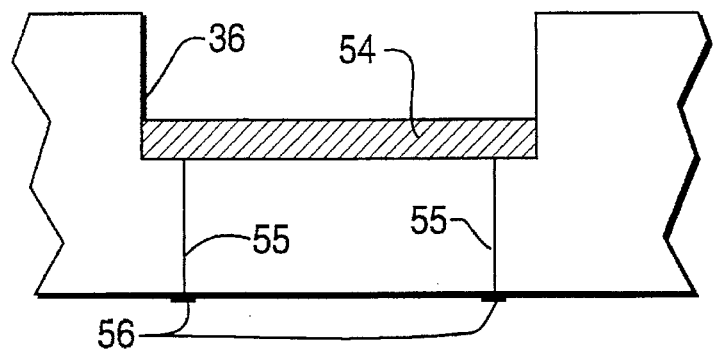
FIG. 4A is a cross sectional view of a well embodiment of a microlaboratory disc of the invention.

Fluid material may be transmitted to the various wells from the first well 36 or from the loading channel 34 by various methods. An external mechanical pumping system 22 that can deliver fluid in reproducible and accurately controlled amounts and that can maintain the purity and sterility of test liquids can be employed. The 205U multi-channel cassette pump available from Watson-Marlow, Inc is a suitable pump. Alternatively, miniaturized mechanical pumps, based on microelectromechanical systems (MEMS) can be used. These miniature pumps may be internal or external to each well 36, 40, 42 and 44. Such pumps have been reported by Shoji et al, "Fabrication of a Micropump for Integrated Chemical Analyzing Systems", Electronics and Communications in Japan, Part 2, 70, pp52–59 (1989). Other suitable pumping means to move fluids through microchannels include electrokinetic pumps as reported by Dasgupta et al, see "Electroosmosis: A Reliable Fluid Propulsion System for Flow Injection Analysis", Anal. Chem. 66, pp1792–1798 (1994), or electrophoresis methods, which require inert metal electrodes, can also be used. In the latter case, a gold electrode can be deposited in the various wells of a module, as shown for example as metal layer 54 in the bottom of the first well 36, as shown in FIG. 4A. The electrode 54 is connected via leads 55 to a circuit or other electrical connection 56.

When large amounts of fluid need to be passed through the connecting channel 38, such as diluents, buffer solutions, rinse solutions and the like, an external mechanical pump 22 in the station 16 will be used to pass these solutions through the channel 38 into the desired well. When smaller amounts of material are required, an on-disk internal pumping system can be used for greater efficiency. Further, prepackaged chemicals sealed in plastic release containers can be deposited in the various wells for particular tests, as required.

Figure 4B:
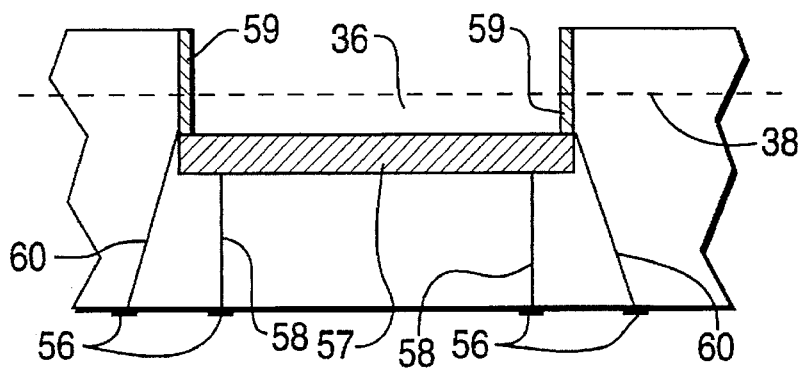
FIG. 4B is a cross sectional view of another well embodiment of a microlaboratory disc of the invention.

In the case where the temperature of a particular well is to be monitored or changed, a means of heating or cooling the well is built into the well, as will be further explained below with reference to FIG. 4B.

The first well 36 in this example is the sample preparation well. A thin film of a suitable metal oxide 57, such as tin oxide or indium tin oxide, is deposited onto the well material and is connected by means of an electrically conductive metal connection 58 to the end or outer edge of the well 36. The tin oxide coating 57 serves as a heater element for the well 36. The well 36 also has a surface bimetal film 59 and leads 60, suitably made of chromel-alumel alloys, forming a thermocouple to measure the temperature in the well when a source of current is applied to the tin oxide coating 57 and to the leads 58. A voltage applied to the well 36 via electrodes 56 deposited on the backside as shown, or preferably on the frontside of the microlaboratory disc 14, regulates the temperature in the well. The amount of current applied can be regulated by the computer 10 in response to the temperature measured through the leads 60.

The first well 36 of the present module 48 also contains a blood affinity binding material, (not shown) such as Leukosorb™ available from Pall Co. and commercially available solutions to lyse the red and white blood cells of the sample and to carry the DNA from the first well 36.

Thus the devices and certain reagents needed for each well will be preformed and loaded into the well or directly pumped into the well from a common source. Fluids can be preloaded into the well either from a reservoir in the station 16 leading to the loading capillary tube 32 connected to the microlaboratory disc 14, or a reservoir and channel into the well may be formed adjacent to the well in which the fluids will be used.

Additional devices can be built into the wells. For example, a means of stirring reactants can also be built into a well using alternating fields. For example, two or more electrodes can be evaporated into each side of a well and connected to external leads, in turn connected to a source of alternating current. The alternating fields will provide reversible magnetic fields to move paramagnetic particles in the wells and to cause, as well, fluid movement in the well.

Figure 5A:
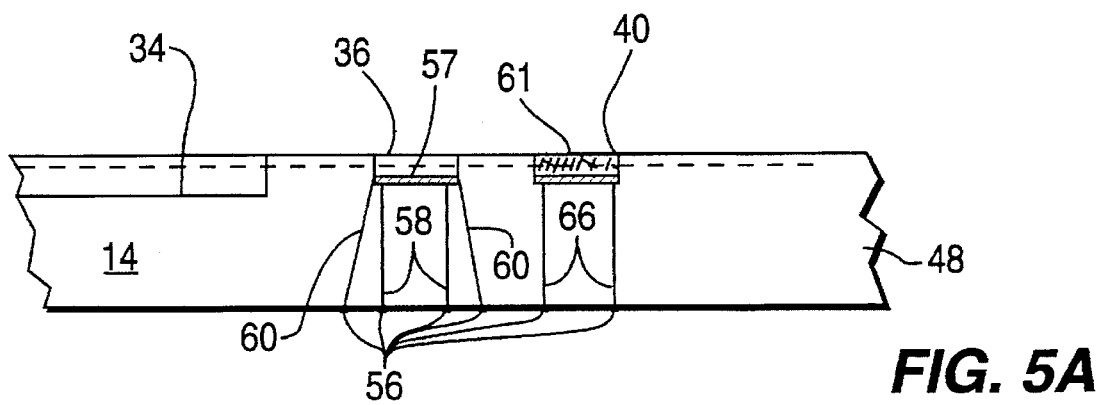
FIG. 5A is a cross sectional view of a portion of a module of a microlaboratory disc illustrating devices in typical wells.

As shown in FIGS. 5A, paramagnetic beads 61 are deposited in the second well 40 of the present module 48, to bind DNA material and to move the DNA to the succeeding wells for amplification, detection and assay. These beads are commercially available for PCR protocols from Bang Laboratories of Carmel, Ind. for example. The well 40 is also connected by means of leads 66 to the electrodes 56.

Figure 5B:
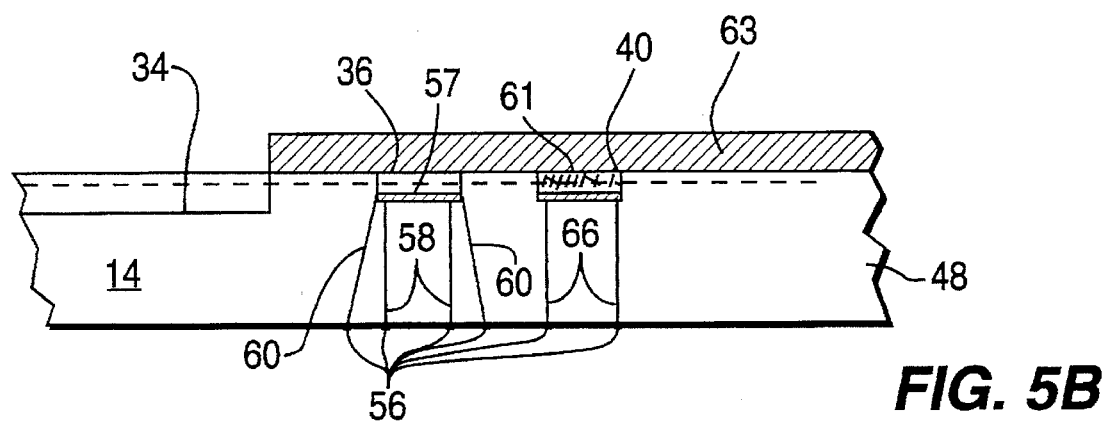
FIG. 5B is a cross sectional view of a portion of a module of a microlaboratory disc covered with a cover plate.

When all of the wells have been prepared and loaded, a glass cover plate 63 is affixed to the microlaboratory disc 14, as shown in FIG. 5B, to complete a capillary structure for the connecting channel 38 and to ensure that fluids in the wells do not evaporate. The cover plate 63 can be made of the same or different material as the microlaboratory disc, but the thermal coefficient of expansion of the cover plate 63 and the material used to make the microlaboratory disc 14 must be similar. The sealing temperature required to seal the cover plate 63 to the disc 14 must also be below the flow temperature of the disk material to prevent distortion of the etched channels and wells. The use of electric fields to seal the cover plate to the disk is suitable because sealing will take place at a lower temperature than the flow temperature, e.g., about 700° C. or less, which is well below the flow temperature of silicon, about 1400° C., or of Corning 7059 glass (about 844° C.), available from Corning Glass Co., for example.

The invention will be further explained in terms of examples that describe different modules for performing different processes, such as assays and syntheses, simultaneously and in parallel. However, the invention is not meant to be limited to the details described therein and additional processes and syntheses can be readily performed by appropriate changes to the number of wells in a module, the devices formed in or adjacent to the wells, the number and type of devices needed to pass fluids into and out of the wells, the number and type of processing-type devices built onto the disc other than the modules, and the like.

EXAMPLE 1

DNA Analysis

The sample fluid is passed into the loading channel 34 or the loading channel 50 as explained above. The sample then moves by application of an electric field or is moved by a pump 22 into the first well 36 through the channel 38, where the separation of the sample, e.g., filtration, lysation and DNA separation, takes place. The first well 36 is fitted with a means of heating and temperature control, as shown in more detail in FIG. 4. A layer of tin oxide 57 is first deposited in the well 36 by CVD. A bilayer film 59 is deposited over the tin oxide film 57 in the well 36, and a metal connection 60 is deposited along a sidewall of the well. Electrodes 56 and 60 are formed on the backside of the microlaboratory disc 14, and leads 58 and 60 connect the thermocouple 59 to the external contacts 56. The current in the leads 58 and the voltage from the leads 60 are monitored and controlled by the computer 10.

The well 36 is also preloaded or post loaded with a blood affinity binding material such as Leukosorb™ media from Pall BioSupport Div. Other commercially available materials can also be used as desired for the same purpose. The amount of Leukosorb B employed depends on the area in the first well 36. The Leukosorb B filters the blood cells from the blood serum sample. A known buffer solution is then passed into the first well 36 by means of the channel 38 in an amount sufficient to assist in lysing and washing the red corpuscles in the sample. A white corpuscle lysis buffer solution, for example a solution of 50 millimoles of KCl, 10 millimoles of Tris HCl having a pH of 8.3, 2.5 millimoles of $MgCl_2$, 0.45% Nonidet P40 and 60 ml of Proteinase K, is then passed into the first well 36 via the channel 38 in an amount sufficient to lyse the white corpuscles. The first well 36 is then heated to 55° C. for fifteen minutes to cause the desired reaction. The cell was then heated to 100° C. for about 10 minutes to inactivate the proteinase K following known procedures.

Figure 6A:
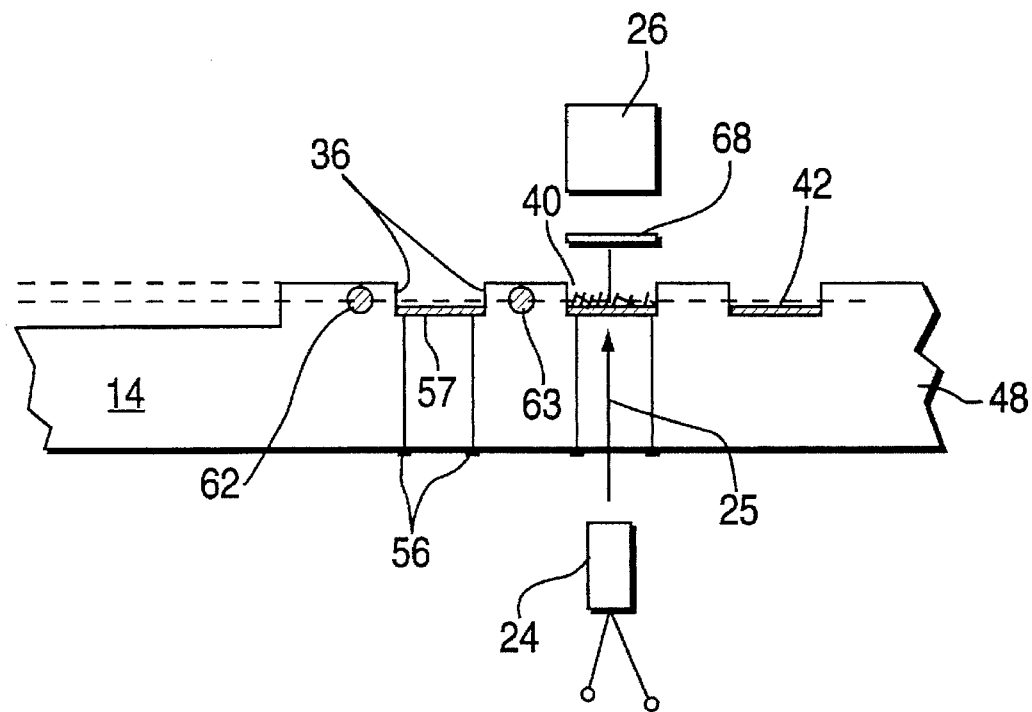
FIG. 6A is a cross sectional view of a microlaboratory disc illustrating additional wells having preformed devices therein together with an optical system interface.
Figure 6B:
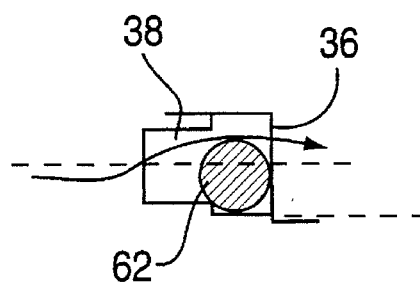
FIGS. 6B and 6C illustrate a valve situate in a channel adjacent to a well in the open and closed positions respectively.
Figure 6C:
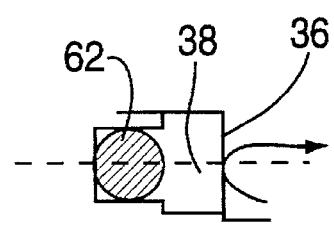

Because of the high temperatures required in the last two steps, a significant vapor pressure may develop in the first well 36, causing a back pressure in both directions—back toward the sample loading channel 34 and forward to the succeeding second well 40. Thus preformed valves 62 and 63 as shown in FIG. 6A, formed of bimetallic materials as described by Jerman et al, "Understanding Microvalve Technology", Sensors, September 1994 pp 26–36 are preloaded into the channel 38. These materials have a thermal expansion mismatch. When the temperature in the well 36 is low, the ball valve 62 is in its normal position permitting free flow of fluids into the well 36, see the arrow shown in FIG. 6B. As the temperature in the well 36 increases, the ball valve 62 moves to a cooler position, as shown in FIG. 6C, blocking the channel 38 and isolating the well 36 from the channel 38, thereby preventing fluids from passing into and out of the first well 36. By proper placement of the well heater 57, the temperature gradient from the heated well 36 will be sufficient to open and close the valves 62, 63, thus eliminating the need for separate electrical, thermal or mechanical control of the valves 62, 63.

However, other means may be employed as desired for closer control of the temperature and pressure in the well 36. A simple design comprises a small micron size sphere 64, such as one made of quartz or polytetrafluoroethylene polymer for example, which may be confined in the channel 38 to act as a conventional check valve, i.e., to prevent backward flow into the channel 38. However, there is no check on the flow forward into the succeeding well 42 with this design, which may be disadvantageous for certain applications and combinations of sequential wells. This check valve 64 can be implemented as an insulating or magnetic sphere, and by application of externally applied electrostatics or magnetic fields, cause the valve to open or close. Such a design will permit closure of the ball valve 64 on demand, permitting control of liquids both forward and backward in the channel 38. Such a design may be particularly advantageous when a synthesis procedure is carried out on the microlaboratory disc 14.

Still referring to FIG. 6A, the prepared and treated blood sample is then transferred to the second well 40 for PCR amplification of the obtained DNA sample from the first well 36. This well 40 contains a layer of paramagnetic beads 61 to bind with the DNA material moved into the well 40. A minimum of about 10 nanograms of DNA are required for this assay. The amount actually in the well 40 can be determined by the electro-optic light source 24 and detector 26 located in the station 16. An optical fiber 25 of the light source 24 is connected to the well 40, and can be an optical fiber 25 of 200, 400 or 600 micron diameter to provide 260 nm radiation for the detection of DNA in this example. Optical fibers transmitting at 250–260 nm are commercially available. The optical fiber 25 of FIG. 6A which is connected to the detector 26 collects and transmits the light measured in the well 40 to an ultraviolet sensitive silicon photodetector 26 having good stability. Suitable detectors include thermoelectrically cooled UV enhanced silicon photodetectors, or miniaturized UV sensitive photomultipliers which are also commercially available. The photomultiplier-type detector has greater sensitivity. The absorbance of DNA is known and is set forth in the Table below.

TABLE

| Species | Absorbance at 260 nm | Concentration, mg/ml |
|---|---|---|
| Double stranded DNA | 1 | 50 |
| Single stranded DNA | 1 | 33 |
| Single stranded RNA | 1 | 40 |

A well known means of assaying DNA is the hybridization technique. The third well 42 is used for this purpose. The well 42 will be fitted by hybridization probes which are unique to the source of DNA and its diagnostic scope. The desired probes may be directly synthesized in the well 42 or commercial sources can be used.

The method most suitable for the microlaboratory array disc 14 for assaying DNA is the use of a non-radioactive tag, which can contain a fluorescent dye, for example for the Phycobiliprotein, or other class of protein. These materials absorb light above 600 nm. A compact solid state laser 24 emitting in the 600–650 nm range situate in the station 16 can be used to produce fluorescence in the tag. The probe in this example will emit above the exciting wavelength of 600 nm, i.e., in the 600–800 nm range. The Phycobiliprotein fluorescent tag agents are commercially available, e.g., $Cy_5$™, from Jackson Immuno-Research Labs. Inc of West Grove Pa. The fluorescence will be detected by means of the detector 26 also in the station 16. A filter 68 will also be inserted between the photomultiplier photodetector 26 and the laser 24 as shown in FIG. 6 to block the laser radiation.

A suitable detector for the fluorescence emitted by the fluorescent tag is one having high sensitivity and optimum long term stability. Other commercially available means for detection of antibodies other than that described above can also be employed. For example, enzymes that form highly colored products, resulting in detection having excellent sensitivity, or chemiluminescent compounds can be employed and detected optically. Radioisotopes can also be used, but their use is being discouraged to prevent adverse effects on the operator of the tests, and they present disposal problems. The light transmission detection system itself is also located in the station 16.

EXAMPLE 2

Immunological Assay

A second example illustrating the design and utility of a microlaboratory disc 114 is shown in FIGS. 7A and 7B and is one suitable for carrying out a plurality of immunological assays, also in parallel. The station 16, sample loading channel 134, and plurality of wells 136, 140, 142 and 144 connected by a channel 138 are similar to those of Example 1, but the materials and processes carried out in the wells, and the number of wells required, are different.

To carry out an immunological assay, a blood sample or other fluid sample of about 100 nanoliters is filtered to obtain a material having sufficient antibodies so that an assay can be determined using standard methods for detection of select antibodies. The microlaboratory disc 114 is able to process 200–1000 samples in parallel.

The initial transfer of a sample to the microlaboratory array 114 is the same as for Example 1. The first well 136 is loaded with preselected bound antibodies on the cell wall, and, by transfer of appropriate reagents and fluid flow control into each well 136 of the module 148, assays can be performed with that antibody. The flow of reagents and solvent will be controlled by the station 16, and the optical detection system 24, 25 and 26 will be set up for transmittance (absorption) measurements.

A series of different antibodies can be placed in additional wells 140, 142, 144 and 146 for sequential testing for various antibodies in successive wells, as shown in FIG. 7B. The number of wells required will be determined by the number of appropriate reagents and the number of antibodies to be tested.

A control means 171 to control the fluid flow of reagents and solvents will be enabled by element 162, which is a switch or valve that controls the flow of fluid into the channel 138 and into the first well 136. For example, a magnetic sphere can form a ball valve 162 by activation of an electric field by means of the computer 10.

As shown in FIG. 7C, a ball valve 162 is fitted into the channel 138 on both sides of the well 136. A source of current 170 is placed adjacent the channel 138 to control the flow into or out of the well 136, and the backside of the microlaboratory disc 114 will have a lead 172 that connects to the driving method employed, such as the computer 10.

EXAMPLE 3

Synthesis of Proteins or Oligonucleotides

Figure 8:
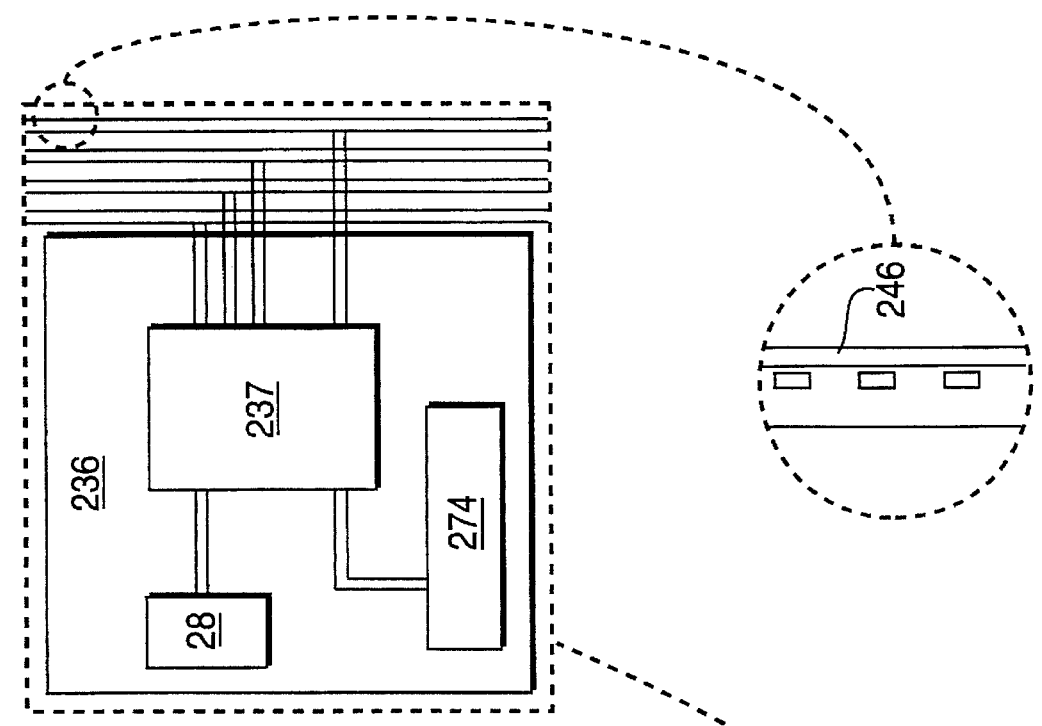
FIG. 8 is a schematic view of another embodiment of a microlaboratory array suitable for carrying out the parallel synthesis of proteins and oligonucleotides.
Figure 8:
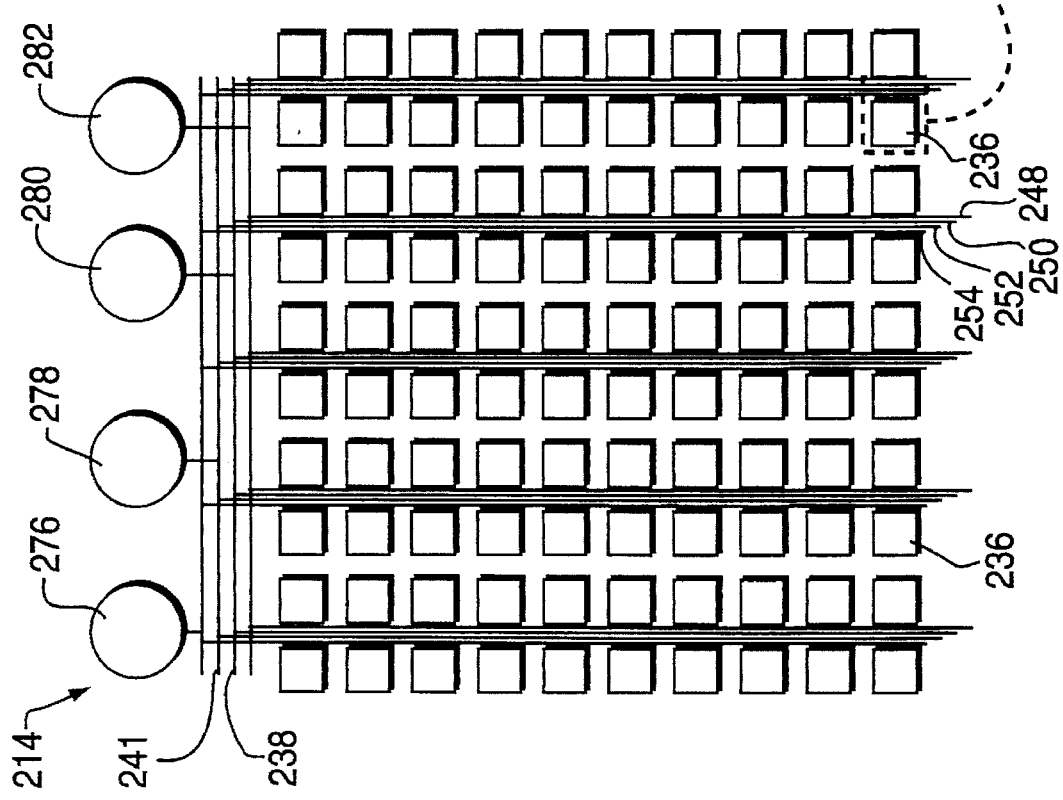

This example, shown in FIG. 8, illustrates a microlaboratory disc 214 that has a modular design that permits the synthesis of a large array of proteins or oligonucleotides in parallel. Such synthesis is a great time saver for drug testing for example, when a whole series of related compounds can be synthesized in each well of an array, and then tested for biologic activity.

For example, the synthesis of solid phase oligonucleotides in a well has been described by Hayakawa et al, "The Allylic Protection Method in Solid-Phase Oligonucleotide Synthesis. An Efficient Preparation of Solid-Anchored DNA Oligomers", J. Am. Chem. Soc., Vol 112, No 5, 1990 pp1691–1696, in a sequence of eight steps:

Step 1: washing the well with acetonitrile ($CH_3CN$)
Step 2: detritylation with 3% $Cl_3CCOOH$—$CH_2Cl_2$
Step 3: washing the well with acetonitrile
Step 4: adding a coupling agent such as 0.1M phosphoramidite-$CH_3CN$ and 0.5M (4-nitrophenyl) tetrazole-$CH_3CN$-THF (tetrahydrofuran)
Step 5: washing the well with acetonitrile
Step 6: capping with $Ac_2O$-2,6-lutidine-THF (1:1:8) and 6.5% 4-(dimethylamino)pyridine (DMAP)-THF
Step 7: oxidizing with 1.1M t-$C_4H_9OOH$—$CH_2Cl_2$
Step 8: washing the well with acetonitrile to remove excess acid.

After the above 8 steps have been carried out in a reaction well 237 using different protected monomers sequentially to build up lengths of oligomers as desired, additional reagents or solvents can be used to remove protective groups used for synthesis prior to disassociating the synthesized oligomers from their support. The various oligomers in each well can then be prepared for screening. A screening cell 274 can also be built into the well 236 as shown in FIG. 8.

In this design, as shown in FIG. 8, a plurality of modules or wells 236 are connected by means of various channels, and a complete synthesis of different compounds will be carried out in a single well 236. The additional features of this microlaboratory 214 design are in the array design which permits controllable and sequential delivery of various reagents and solvents to each of the wells in parallel. The reagents and solvents can be stored in reservoirs 276, 278, 280 and 282 built into the microlaboratory array, or they may be delivered from reservoirs external to the microlaboratory array, for example in the station 16, as desired.

Figure 9:
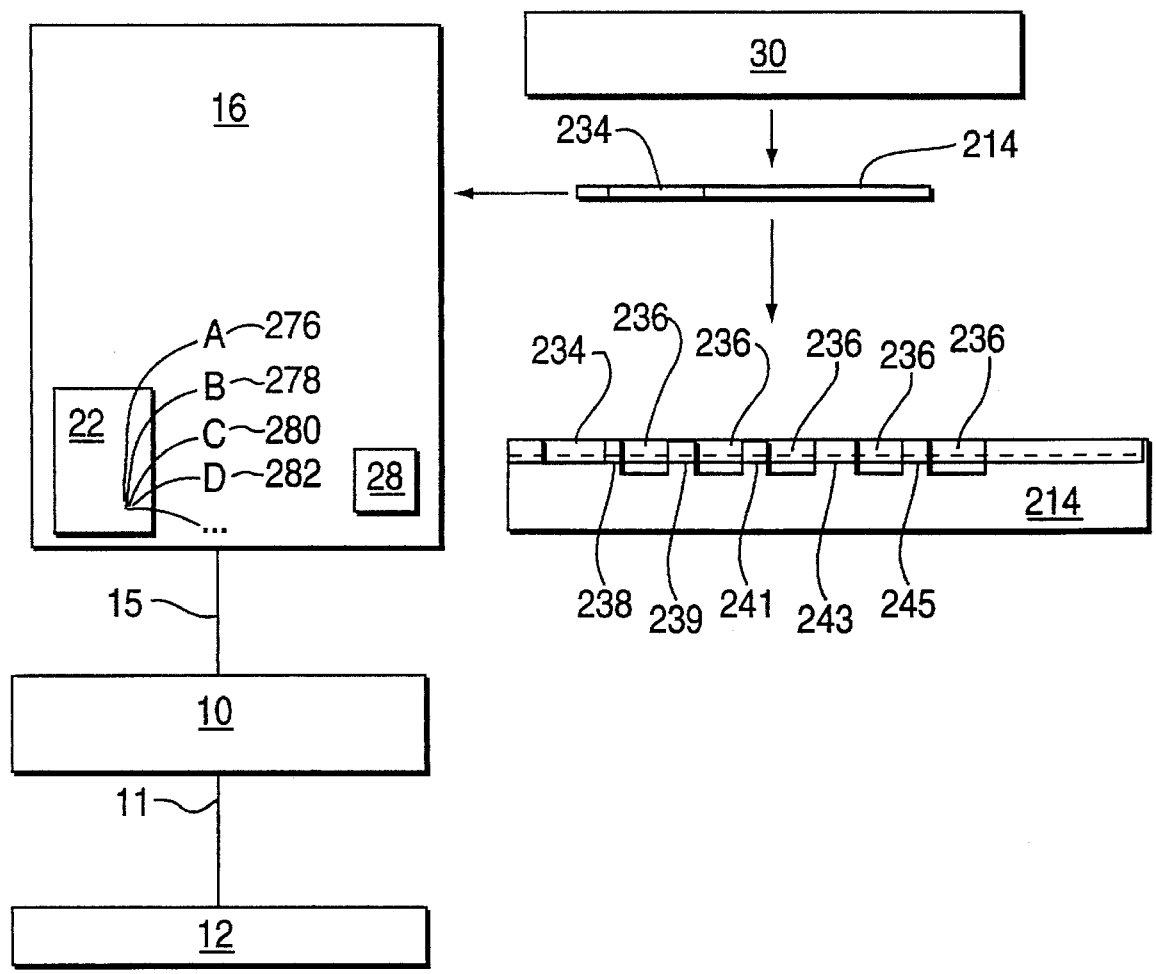
FIG. 9 is a schematic view illustrating a modified station for the system of FIG. 8.

FIG. 8 illustrates a suitable design for a microlaboratory array wherein reservoirs 276, 278, 280, 282 for reagents and solvents are included in the substrate; and FIG. 9 is a partial schematic view of a system for synthesis wherein reservoirs 276, 279, 280 and 282 are added to the station 16, each connected to a fluid pump 22 for delivery to the wells of each module.

Each well in this array has a plurality of horizontal channels 238, 239, 241, 243, 245 entering and exiting each well 236, and a plurality of vertical channels 248, 250, 252 and 254, each of which leads to a different reservoir. The reagents and solvents move along the channels by means of gating electrodes, as shown in FIG. 7C, that move the fluid along the channels.

As shown in FIG. 8, reagents are delivered in parallel from the different reservoirs 276, 278, 280 and 282 into channels 238, 239, 241, 243 respectively. Each of these channels has a built in gating electrode 162 to monitor the flow of fluids from the different reservoirs into the wells 236 as required. In this embodiment, since all of the synthesis reactions take place in a single well 236, each well 236 is placed in an array and one or more channels lead into and out of each well 236 for delivery of reagents in parallel or serially. Thus instead of a modular design, when sequential wells are used for the various steps of the process being carried out, an array of like wells 236 is used but a different chemical synthesis is carried out in each well. The overall design is no longer a plurality of modules, but an array of wells, and hundreds of compounds can be synthesized on a single microlaboratory substrate 214.

After all the synthetic steps are completed, the syntheses can be monitored or screening can be conducted by passing a sample into a screening cell 274 which can be built into the well 236.

This type of array can be used to synthesize a large number of oligomers and peptides which follow a repetitive sequence of steps as above.

EXAMPLE 4

Synthesis of Small Molecules

This microlaboratory array of this example 314 is also designed to produce an array of small molecules, such as a plurality of different alkyl compounds. Since such an array depends on the delivery of a different starting material for each compound, e.g., methyl-substituted, ethyl-substituted, n-propyl-substituted, iso-propyl substituted compounds and the like, a large array of starting material reservoirs or supply sources will be needed so that a different starting material will be delivered to each well. The reactants and solvents and reaction conditions, e.g., heating, will be delivered as required, see Examples 1 and 2.

Figure 10:
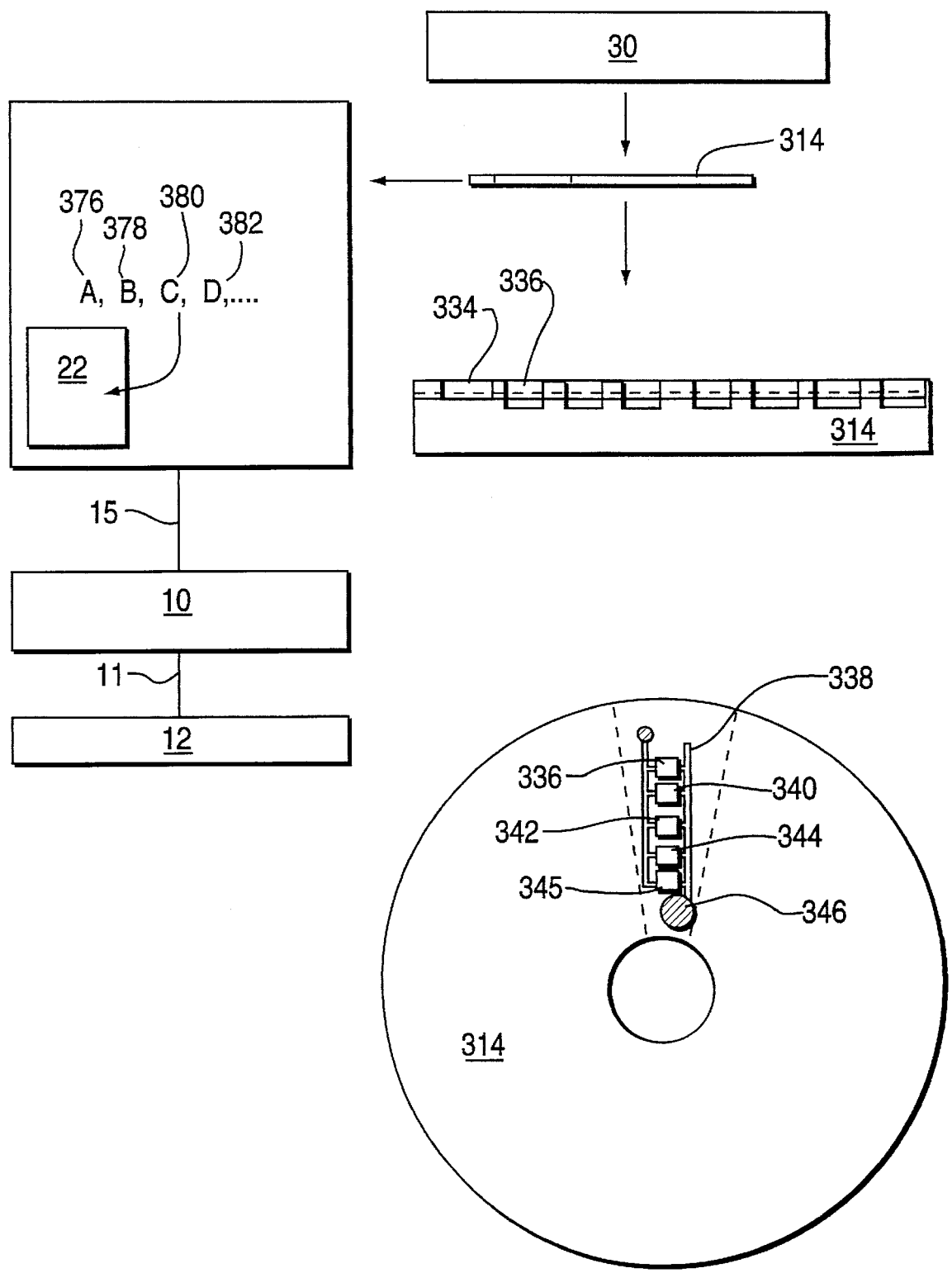
FIG. 10 is a schematic view of a further embodiment of a microlaboratory arrays suitable for carrying out the synthesis of a large number of small molecules in parallel.

For example, the synthesis of an array of 1,4-benzodiazepine compounds can be carried out as follows:

Step a): bind the starting material 4-[4-benzoyl-6-chloro-2-fluorenylmethoxy carbonylaminobenzoyloxymethyl]phenoxyacetic acid onto aminomethyl resin or its equivalent as a coating material on the channel surfaces;

Step b): remove the 9-fluorenyl methoxy carbonyl (FMOC) protective group from the bound material using piperidine in DMF, supplied from station reservoir 376 into the wells 338;

Step c): couple an amino acid, alpha-N-FMOC-amino acid (fluoride) from a second reservoir 378 in the well 338;

Step d): remove the FMOC protective group by moving piperidine in DMF through the wells 338;

Step e): forming a cyclic benzodiazepine derivative with 5% acetic acid in DMF from a third reservoir 380 in wells 340;

Step f): alkylate with a lithium salt in DMF from a station reservoir 382 in wells 342 that are fitted with a control for pumps and switches, monitored by the computer 10, to deliver different alkylating agents to the microlaboratory array 314 selectively, as shown in FIG. 10. Thus the "reservoir" for the alkylating agent is in reality a source of a whole series of alkylating agents that can be delivered selectively to a particular well in the array. The fluid delivery to the wells can be controlled by a control means 171 as shown in FIG. 7C. In this manner, a different compound is made in each well. However, since each compound requires several steps for synthesis of the various compounds, several wells may be employed to synthesize each of the compounds and this microlaboratory disc 314 may comprise a plurality of modules as well.

Figure 11A:
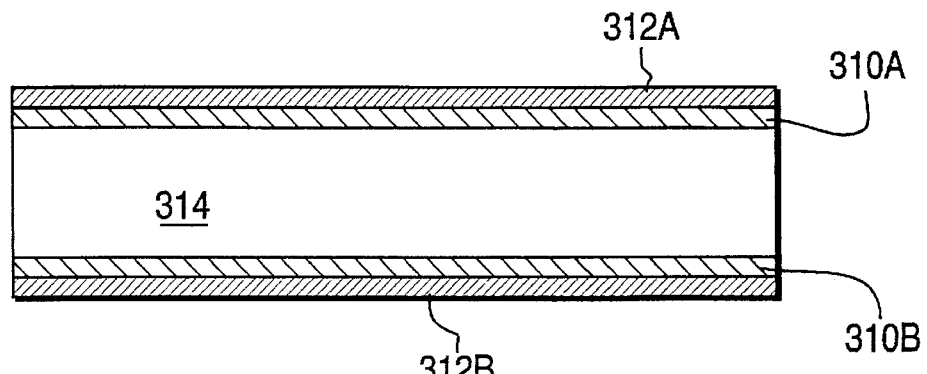
FIGS. 11A, 11B and 11C are cross sectional views illustrating the steps needed to form cross over channels in the substrate.
Figure 11B:
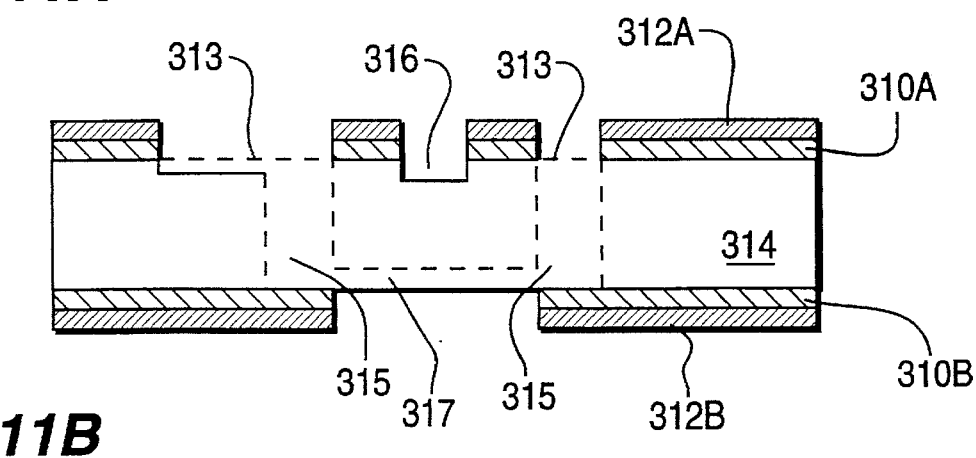
Figure 11C:
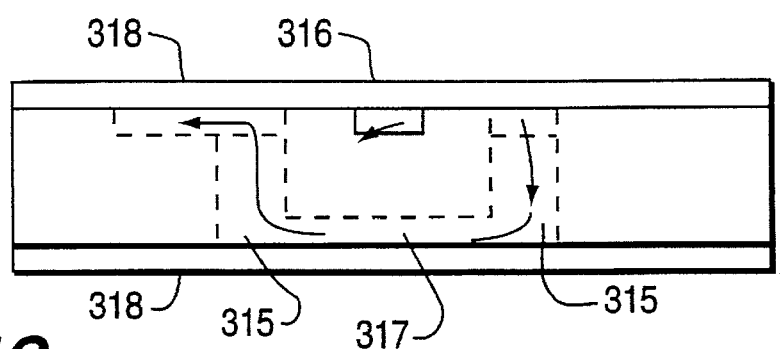
Figure 11D:
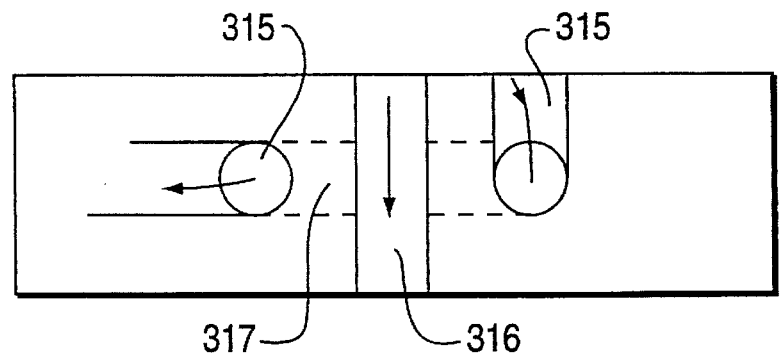
FIG. 11D is a top view of a cross-over channel in the substrate.

Another feature of the present invention is the fabrication of cross-over channels that permit high density arrangements of wells/modules in an array that can be serviced from more than one channel either to transmit fluids into the well, out of the well, or to transmit the material being treated to a succeeding well; and wherein the channel or channels connected to a particular reservoir do not intersect with channel(s) connected to other reservoirs so that reagents and solvents are controllably mixed in the wells. Such cross over channels can be formed in the following manner. Referring to FIG. 11A, a substrate 314 is coated on both sides with a first chromium-gold layer 310A and 310B and a photoresist layer 312A and 312B as described above. The photoresist layer 312A is exposed and developed to form openings 313 for a first channel and the chromium layer 312A is etched away in the opening 313. The glass substrate 314 is then etched through to the chromium-gold layer 310B forming openings 315. The photoresist layers 312A and 312B are re-exposed and developed to form a second pair of openings 316 and 317 on each side of the glass substrate 314. However, the second opening 316 in the layer 312A is perpendicular to the opening 317 in the layer 312B, which is parallel to the openings 315 made originally. The opening 317 is formed adjacent to the openings 315 already formed in the glass substrate 314, as shown in FIG. 11B. The glass substrate is next etched to open a passage between the openings 315 and 317, thereby forming a continuous channel that extends through the glass substrate 314 and across beneath the second perpendicular channel 316 as shown in FIG. 11C. A cover plate 318 will be bonded to both sides of the substrate 314 to enclose the cross-over channels 315-317-315 and 316 on both sides of the substrate 314 and to complete the substrate having crossing but non-intersecting channels whereby a first portion of each such a channel is situated horizontally at a first vertical level within the substrate, at an endpoint of the first portion a second portion of the channel extends vertically to a second vertical level within the substrate and connects to a third portion of the channel that extends the channel in a horizontal dimension, and whereby the change in the vertical level of the channel allows the channel to avoid intersecting one or more other channels within the substrate as shown in FIG. 11D.

Figure 12:
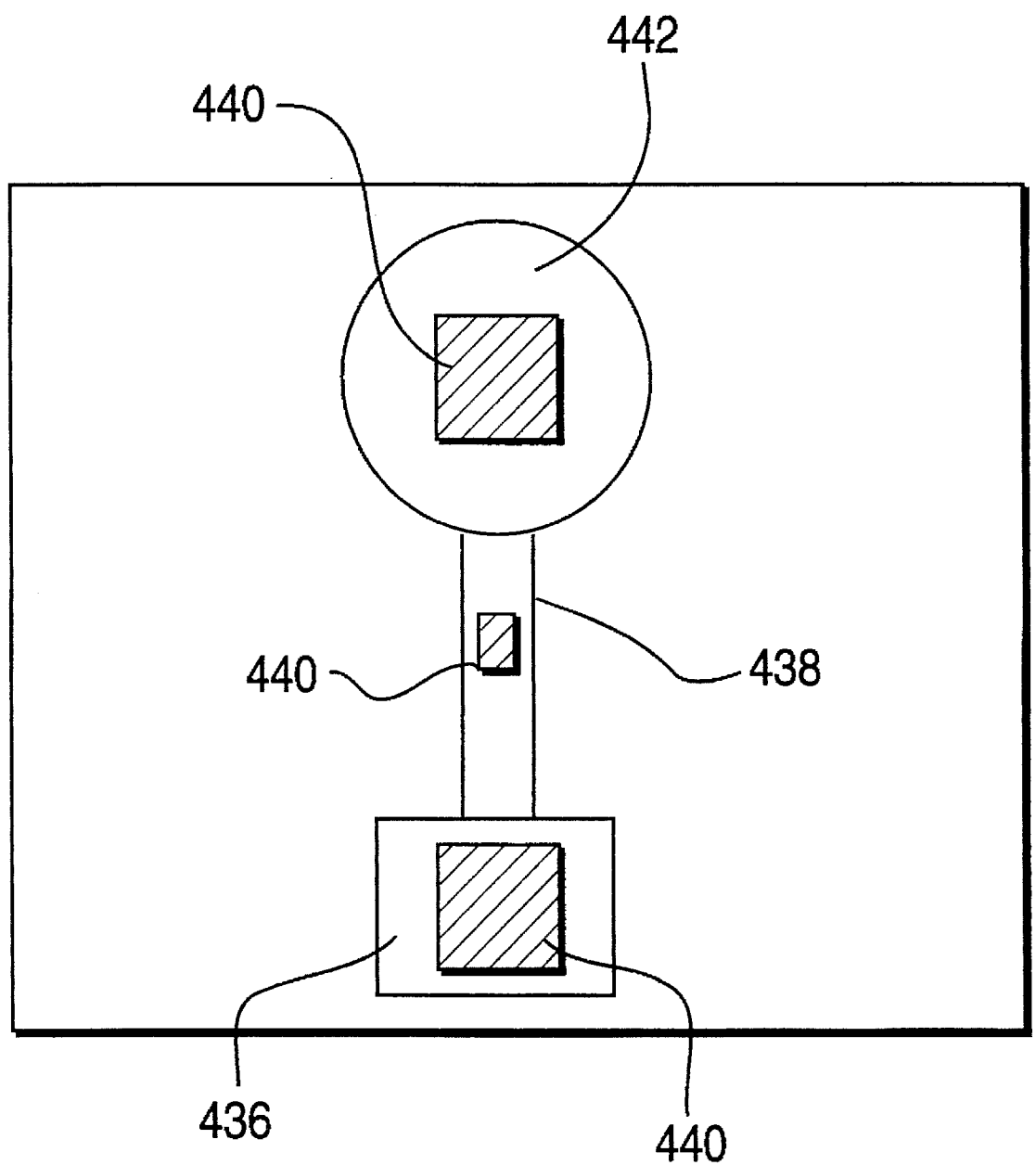
FIG. 12 is a top view of a channel "gate" electrode to control flow in a channel by electro-osmosis.

In order to move materials from the reservoirs into each well of the array, the material from the reservoir can be injected into one or more the channels 316. The material in each channel moves along the channel 316 via capillary action. However, since one or more of the reactions may require more or less time depending on the amount of material employed, or to compensate for faster or slower movement of certain materials through the channels, the material flow in the channels preferably can be controlled by means of a drain electrode deposited in each well, and in each reservoir and in the channel leading from the reservoir to the respective well. By creating a negative charge at the well, the flow along the channel will be stopped, thereby permitting control of reagent feed into each well. This is shown in FIG. 12 which is a top view which shows a drain electrode 440 deposited in the well 436, in a channel 438, and in the reservoir 442.

A desired microlaboratory array can be designed to carry out a wide variety of tests and syntheses rapidly, reliably, inexpensively and in parallel, greatly reducing costs. Further, because of the integration of the microlaboratory array and means of regulating, measuring and recording information, records of tests and screening-data are reliably generated and stored. Since genetic screening may become the blood tests of the future, the ability to perform DNA testing rapidly, reliably and at low cost, will be highly advantageous.

Thus although the present invention has been described in terms of particular examples, the invention is not meant to be limited to the details given above. One skilled in the art can readily substitute different mechanical or electrical means of transferring fluids through the channels and wells, of substituting various bonding agents, starting materials and reagents to perform different assays and syntheses, and to form the wells, channels and devices in the channels and wells by alternate methods. For example, integrated circuits can also be employed to move fluids and monitor and measure wells of the arrays using conventional semiconductor techniques and materials. Semiconductor technology can also be used to form leads, electrodes and the like. Thus the invention is only to be limited by the scope of the following claims.

We claim:

1. A method of synthesizing a plurality of proteins or oligonucleotides in parallel which comprises, providing a substrate having a plurality of wells, each well connected to a plurality of reservoirs for reagents or solvents, which reservoirs are formed in the substrate, the reservoirs connected to said wells by one or more channels, wherein the channel(s) connected to a particular reservoir do not intersect with channel(s) connected to other reservoirs so that reagents and solvents are controllably mixed in the wells;

moving reagents or solvents in sequence from said reservoirs along said channels and into and out of said wells by means of electrokinetic pumps each connected to a driver means; and reacting said reagents to form a plurality of proteins or oligonucleotides.

2. The method according to claim 1, wherein a first portion of each said channel, connected to a reservoir formed in the substrate, is situated horizontally at a first vertical level within the substrate, at an endpoint of the first portion a second portion of the channel extends vertically to a second vertical level within the substrate and connects to a third portion of the channel that extends the channel in a horizontal dimension, and whereby the change in the vertical level of the channel allows the channel to avoid intersecting one or more other channels within the substrate.

3. A method according to claim 1 comprising reacting a starting material and a coupling agent in each well, thereby forming a product in each well, wherein the coupling agent in at least two wells differ from each other.

4. A method of synthesizing a plurality of different compounds in parallel which comprises, providing a substrate having a plurality of wells, each well connected to a plurality of reservoirs for reagents or solvents, which reservoirs are formed in the substrate, the reservoirs connected to said wells by one or more channels, wherein the channel(s) connected to a particular reservoir do not intersect with channel(s) connected to other reservoirs so that reagents and solvents are controllably mixed in the wells;

adding a starting material having a protecting group to plurality of the wells;

removing the protecting group from the starting material; and adding a coupling agent to each well from a reservoir by means of a channel connected to said reservoir and to said well; thereby producing a plurality of different compounds.

5. The method according to claim 4, wherein a first portion of each said channel, connected to a reservoir formed in the substrate, is situated horizontally at a first vertical level within the substrate, at an endpoint of the first portion a second portion of the channel extends vertically to a second vertical level within the substrate and connects to a third portion of the channel that extends the channel in a horizontal dimension, and whereby the change in the vertical level of the channel allows the channel to avoid intersecting one or more other channels within the substrate.

6. A method according to claim 4 wherein fluid materials are moved into and out of each well by means of a drain electrode in each well, channel and reservoir, wherein said drain electrode is connected to a driving circuit.

7. A method according to claim 1 wherein the substrate is dielectric substrate.

8. A method according to claim 7 wherein the substrate is a high melting temperature glass.

9. A method according to claim 8 wherein the high melting temperature glass has a flow temperature of about 700 degrees Celsius or more.

10. A method according to claim 3 for synthesizing an oligonucleotide further comprising capping the product with a capping agent and oxidizing the product with an oxidizing agent, thereby forming the oligonucleotide.

11. A method according to claim 4 wherein the coupling agent is moved by means of an electrokinetic pump.

12. A method according to claim 4 wherein the substrate is a dielectric substrate.

13. A method according to claim 12 wherein the substrate is a high melting temperature glass.

14. A method according to claim 13 wherein the high melting temperature glass has a flow temperature of about 700 degrees Celsius or more.

15. A method according to claim 4 wherein at least two wells have a different coupling agent added thereto.

16. A method according to claim 4 wherein the plurality of compounds are proteins or oligonucleotides.

17. A method of synthesizing a plurality of different compounds comprising:

a) providing substrate having an array of at least one hundred wells that each have a connection to two or more reservoirs, which reservoirs are formed in the substrate, the connections being provided by channels, which channels are formed in the substrate, wherein the channels connecting the wells to reservoirs would intersect but for crossovers formed by a plurality of channels, whereby a first portion of each such a channel is situated horizontally at a first vertical level within the substrate, at an endpoint of the first portion a second portion of the channel extends vertically to a second vertical level within the substrate and connects to a third portion of the channel that extends the channel in a horizontal dimension, and whereby the change in the vertical level of the channel allows the channel to avoid intersecting one or more other channels within the substrate;

b) adding a starting material having a protecting group to the wells;

c) removing the protecting group from the starting material; and d) adding a coupling agent to each well from a reservoir by means of a channel connected to the reservoir and the well, thereby producing a plurality of different compounds.

18. A method according to claim 17 wherein the coupling agent is moved by means of an electrokinetic pump.

19. A method according to claim 17 wherein the substrate is a dielectric substrate.

20. A method according to claim 19 wherein the substrate is a high melting temperature glass.

21. A method according to claim 20 wherein the high melting temperature glass has a flow temperature of about 700 degrees celsius or more.

22. A method according to claim 17 wherein at least two wells have a different coupling agent added thereto so that the coupling agent is at least two wells differ from each other.

23. A method according to claim 17 wherein the compounds are proteins or oligonucleotides.

24. A method according to claim 17 wherein the array comprises at least ten rows by at least ten columns of wells.

* * * * *